Aug. 8, 1939. C. MALLERIN Plant Pat. 337
ROSE PLANT
Filed Nov. 16, 1938
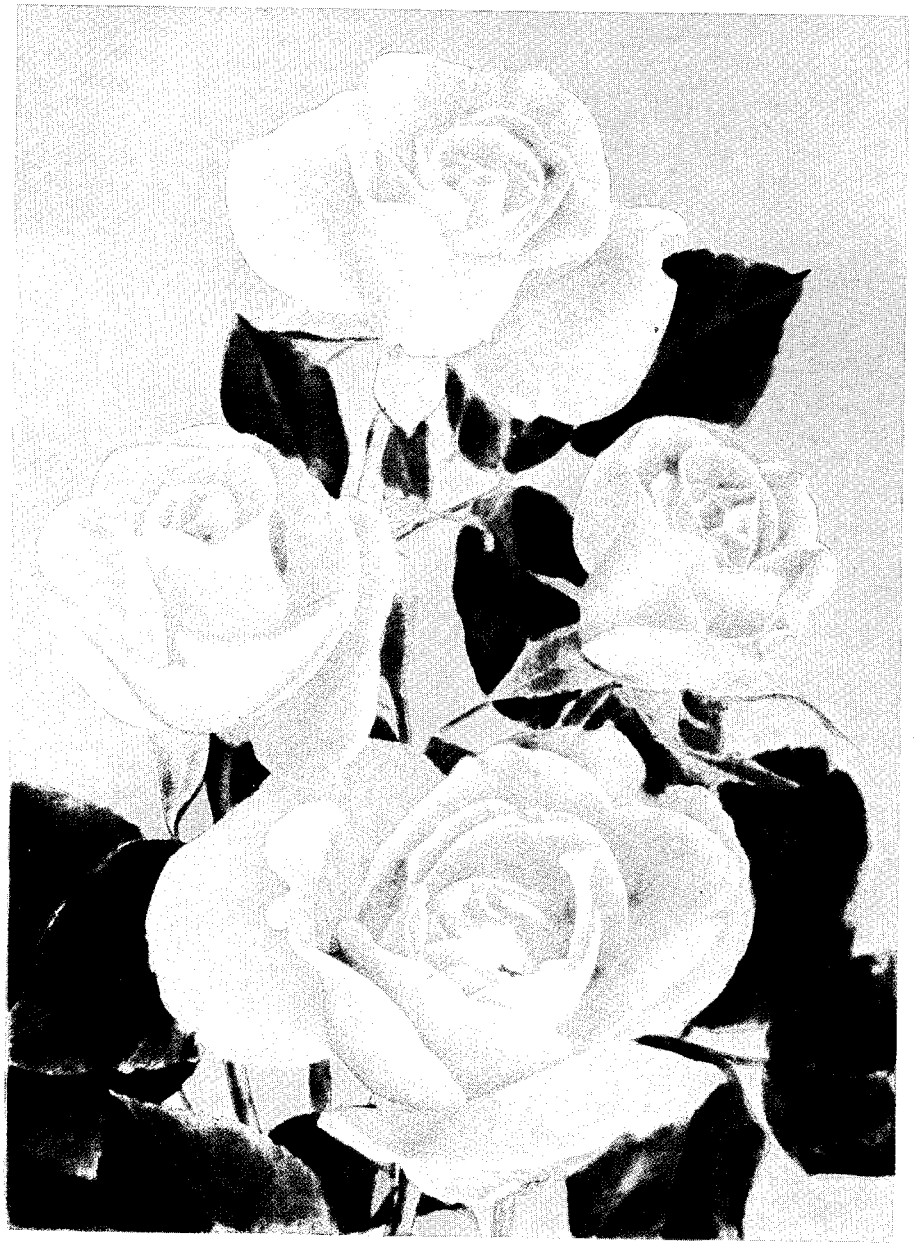
Inventor
C. Mallerin
By Robb & Robb
Attorneys

UNITED STATES PATENT OFFICE

337

ROSE PLANT

Charles Mallerin, Varces, France, assignor to The Conard-Pyle Company, West Grove, Pa.

Application November 16, 1938, Serial No. 240,825

1 Claim. (Cl. 47—61)

The present invention relates to a new and distinct variety of rose plant useful as a garden and cut rose, resulting from a cross between Rochefort and an unnamed seedling of Austrian Copper, and displaying a wide range of differences between itself and any of the present-known roses.

The important characteristics of the plant itself are its extraordinary vigor, the leathery nature and deep green color of the foliage evidencing its great vigor.

The primary features of novelty and distinctiveness, however, are found in the bud of this new rose, which shows the extraordinary and unique quality of being very high and long and at the same time having the urnshape. The term "urnshape" is used in this connection to define the form of a bulging base, leading up to a narrowing neck, and above that the outwardly flaring lips of the petals.

These unusual characteristics as to form and the color of bud and flower, combined with the habit of growth and quality of texture of its make-up, lead me to state that the plant is clearly distinguished from any of the other known roses.

This new variety has been asexually reproduced and its characteristics hereinafter described have been found to be fixed.

The following is a detailed description of the new variety, in which general dictionary color terminology is employed except where otherwise specified.

Parentage:
*Seed parent.*—Rochefort.
*Pollen parent.*—Unnamed seedling of Austrian Copper.

Classification:
Hybrid Tea.

*Flower*

Blooming habit:
Continuous.

Bud:
*Size.*—Medium.
*Form.*—Long pointed; later urnshaped.
*Color.*—Deep coral.
*Sepals.*—Standing outward from bud, some about half as long as bud; others longer than bud, some pointed, others forming a leaflet on tip.
*Calyx.*—Urnshaped.
*Peduncle.*—Light green, strong and smooth.
*Opening.*—Opens well, does not ball.

Bloom:
*Size when fully open.*—3½ to 4 inches.
*Borne.*—Singly.
*Stems.*—Medium length.
*Form.*—Urnshaped, loose.
*Petalage.*—25 to 30 petals.

The following is a color description in accordance with the Ridgway Color Standard and made from a rose grown in a greenhouse during the month of April, 1939, at West Grove, Pa.:

*Color.*—Outside petal: outside surface—Nopal Red, Plate 1; inside surface—more intense and brilliant than Ridgway Scarlet Red. Intermediate petal: outside surface—Rose Doree; inside surface—Begonia rose. Inner petal: outside surface—Rose Doree; inside surface—Begonia rose.

The following was made from a rose that was open for three days in a greenhouse during the month of April, 1939, at West Grove, Pa.:

*Color.*—Outside petal: outside surface—Hermosa Pink to Shrimp Pink, Plate 1; inside surface—more brilliant than Deep Rose Pink, Plate XII. Inside petal: outside surface—Shrimp Pink; inside surface—Rose Pink to Deep Rose Pink.
*General color effect.*—Newly opened flower—Begonia Rose, Plate 1. Three days open—Rose Pink to Deep Rose Pink, Plate XII.

Petals:
*Texture.*—Leathery.
*Appearance.*—Metallic.
*Form.*—Pear-shaped.
*Arrangement.*—Loosely formed.
*Persistence.*—Drop off cleanly.
*Fragrance.*—Very slight.
*Lasting quality.*—Fair to long lasting.
*Behavior.*—Drops off cleanly—"blues" slightly.

Genital organs:
*Stamens, anthers.*—Average; color—lemon; arrangement—normal.
*Stamens, filaments (threads).*—Uneven length; color—amber.
*Pollen.*—Yellow.
*Styles.*—Normal.
*Stigmas.*—Normal.
*Ovaries.*—Normal.

Fruit:
No fruit observed as yet.

*Plant*

Form:
Bush.

Growth:
Strong, slightly sprawly.

Foliage:
*Leaflets to compound leaf.*—Five.
*Size.*—Medium.
*Quantity.*—Abundant.
*Colors.*—Rich green; sometimes bronzy.
*Shape.*—Oval.
*Texture.*—Leathery.
*Edge.*—Serrated.
*Serration.*—Uneven.
*Ribs and veins.*—Ordinary.
*Leaf stem.*—Color—light green; under side—some smooth, others prickly.
*Stipules.*—Medium bearded.
*Disease resistance.*—Subject to blackspot.

Wood:
*New wood.*—Reddish green.
*Old wood.*—Light green.

Thorns:
*Quantity.*—Numerous.
*Form.*—Slightly hooked, broad base with tip opposite base of thorn.
*Color when young.*—Reddish green.
*Position.*—Irregular.
*Prickles.*—None.
*Short needles.*—A few on new wood only.

I claim:

A new and distinct variety of Hybrid Tea rose, characterized as to novelty by its extraordinary vigor, the leathery and deep green foliage, the urnshape and distinctive coloring of its bud and flower, substantially as shown and described.

C. MALLERIN.